United States Patent
Cheng et al.

(10) Patent No.: US 11,143,585 B2
(45) Date of Patent: Oct. 12, 2021

(54) PHOTOELECTRICAL DEVICE FOR CONCENTRATION DETECTION, METHOD FOR CONCENTRATION DETECTION THEREOF AND METHOD FOR TESTING AN ANTIBIOTIC SUSCEPTIBILITY ON BACTERIA

(71) Applicant: National Applied Research Laboratories, Taipei (TW)

(72) Inventors: I-Fang Cheng, Taipei (TW); Tzu-Ying Chen, Taipei (TW); Yi-Ling Chen, Taipei (TW)

(73) Assignee: National Applied Research Laboratories, Taipei (TW)

( * ) Notice: Subject to any disclaimer, the term of this patent is extended or adjusted under 35 U.S.C. 154(b) by 173 days.

(21) Appl. No.: 16/234,597

(22) Filed: Dec. 28, 2018

(65) Prior Publication Data

US 2020/0209135 A1 Jul. 2, 2020

(51) Int. Cl.
*B03C 7/02* (2006.01)
*B03C 7/00* (2006.01)
(Continued)

(52) U.S. Cl.
CPC .......... *G01N 15/0656* (2013.01); *C12Q 1/18* (2013.01); *G01N 2015/0693* (2013.01)

(58) Field of Classification Search
None
See application file for complete search history.

(56) References Cited

U.S. PATENT DOCUMENTS 4,981,362 A 1/1991 deJong et al.
5,166,755 A * 11/1992 Gat .......................... G01J 3/02
250/226

(Continued)

FOREIGN PATENT DOCUMENTS

TW I685656 B 2/2020

OTHER PUBLICATIONS

I-Fang Cheng, Hsiao-Lan Yang, Cheng-Che Chung and Hsien-Chang Chang, "A rapid electrochemical biosensor based on an AC electrokinetics enhanced immuno-reaction," Analyst, 2013, vol. 138, 4656-4662, The Royal Society of Chemistry, pp. 4656-4658.

(Continued)

*Primary Examiner* — Neil N Turk

(57) ABSTRACT

A photoelectrical device for detection of bacterial cell density includes a substrate, a driving electrode layer, an AC power source and a photoelectric conversion layer. The driving electrode layer is disposed on the substrate and includes a central electrode and a peripheral electrode pattern surrounding the central electrode. A fluid sample is disposed on the driving electrode layer. The AC power source is electrically connected to the driving electrode layer, and used to produce a non-uniform alternating electric field in the fluid sample on the driving electrode layer for driving the target bioparticles to gather up on the central electrode to form a particle cluster. The photoelectric conversion layer is used for receiving a light detecting beam after passing through the particle cluster and outputting an electric current based on the optical density of light detecting beam. The electric current changes as a concentration of the target bioparticles changes.

7 Claims, 10 Drawing Sheets

(51) Int. Cl.
*B03C 5/02* (2006.01)
*B03C 5/00* (2006.01)
*G01N 15/06* (2006.01)
*C12Q 1/18* (2006.01)

(56) References Cited

U.S. PATENT DOCUMENTS

| | | | | |
|---|---|---|---|---|
| 5,653,939 | A * | 8/1997 | Hollis | B01J 19/0046 |
| | | | | 204/456 |
| 6,225,059 | B1 * | 5/2001 | Ackley | B01J 19/0046 |
| | | | | 257/E21.43 |
| 6,545,759 | B1 * | 4/2003 | Hartman | G01N 21/45 |
| | | | | 356/477 |
| 7,615,762 | B2 | 11/2009 | Satyanarayana et al. | |
| 2006/0197960 | A1 * | 9/2006 | Bazylenko | G01N 21/648 |
| | | | | 356/491 |
| 2013/0008789 | A1 * | 1/2013 | Ronaghi | B01L 3/502761 |
| | | | | 204/451 |
| 2014/0083855 | A1 * | 3/2014 | Cheng | B03C 5/026 |
| | | | | 204/547 |

OTHER PUBLICATIONS

I-Fang Cheng, Tzu-Ying Chen, and Wen-Cheng Chao, "Increasing local density and purity of molecules/bacteria on a sensing surface from diluted blood using 3D hybrid electrokinetics," Biomicrofluidics, vol. 10, 034116, (2016), AIP Publishing, pp. 1 and 4.

* cited by examiner

PHOTOELECTRICAL DEVICE FOR CONCENTRATION DETECTION, METHOD FOR CONCENTRATION DETECTION THEREOF AND METHOD FOR TESTING AN ANTIBIOTIC SUSCEPTIBILITY ON BACTERIA

FIELD OF THE INVENTION

The present invention relates to a particle/nanoparticle concentration detection device and a method for particle/nanoparticle concentration detection thereof and a method for testing an antibiotics susceptibility on bacteria, and more particularly to an photoelectrical device capable of detecting a concentration of bioparticles and a method for concentration detection thereof and a method for testing an antibiotics susceptibility on bacteria by using the photoelectrical device, wherein the bioparticles include cells, microorganisms or biomolecules.

BACKGROUND OF THE INVENTION

Current biotechnology has developed the use of optical analysis instruments to detect bacteria. The common optical analysis instruments are UV Visable spectrophotometer and turbidity meter. However, whether the spectrophotometer or the turbidity meter, both can only detect purified samples and cannot directly detect mixture samples such as blood and urine.

Secondly, spectrophotometers such as ultraviolet spectrophotometer, visible light spectrophotometer and turbidity meter also have concentration limitations on detecting bacteria. In detail, the concentration of a sample to be detected needs to be greater than $10^8$ CFU/ml (Colony-Forming Unit) so as to be possible of being detected by the spectrophotometer or turbidity meter. In addition, the signal detected from a sample with a concentration of about $10^8$ CFU/ml is not very significant. Although the ultraviolet spectrophotometer and visible light spectrophotometer can measure up to about $10^6$ CFU/ml, the instrument costs are high and the equipments are huge, which limit their application fields. Therefore, for samples having a concentration of less than $10^8$ CFU/ml, the above-mentioned optical analysis instruments (i.e., spectrophotometer and turbidity meter) cannot easily detect the concentration. Thus, when the above optical analysis instruments are practically used for the bacteria detection, it takes more than one day for sub-culturing and incubating the bacteria in order to remove the blood cells/somatic cells and increase the bacterial concentration so that the optical analysis instruments are capable of detecting the sample concentration.

SUMMARY OF THE INVENTION

A main object of the present invention is to provide a photoelectrical device for concentration detection that can detect the concentration of a relatively lower amount of bioparticles in a suspension more rapidly than the above conventional optical analysis instruments due to significantly shortend the incubation period.

A main object of the present invention is to provide a method for concentration detection that can be performed by the above-mentioned photoelectrical device.

The photoelectrical device for concentration detection provided by the present invention is adapted to detect a concentration of a plurality of target bioparticles in a fluid sample through a light detecting beam (focused beam is not required). The photoelectrical device includes a substrate, a driving electrode layer, an AC power source and a photoelectric conversion layer. The substrate is located on a path of the light detecting beam. The driving electrode layer is disposed on the substrate and includes a central electrode and a peripheral electrode pattern located around the central electrode. The central electrode is not in contact with the peripheral electrode pattern, and the central electrode is located on the path of the light detecting beam. The fluid sample is adapted to be disposed on the driving electrode layer. The AC power source is electrically connected to the driving electrode layer and used to generate a non-uniform alternating electric field in the fluid sample on the driving electrode layer, which drives the target bioparticles to gather up on the central electrode to form a particle cluster. The photoelectric conversion layer is located on the path of the light detecting beam and used to receive the light detecting beam after passing through the particle cluster. The photoelectric conversion layer outputs an electric current based on the light detecting beam, and the electric current changes as a concentration of the target bioparticles changes.

In a preferred embodiment of the present invention, the above-mentioned photoelectrical device further includes a measurement electrode pattern. The measurement electrode pattern is connected to the photoelectric conversion layer and used to transmit an electric current.

In a preferred embodiment of the present invention, the above-mentioned measurement electrode pattern includes a pair of measurement electrodes that are not in contact with each other, and the measurement electrodes have a spiral shape or a finger-intersecting shape.

In a preferred embodiment of the present invention, a material of the above-mentioned photoelectric conversion layer includes metallic oxides or silicon having photoelectrical characteristics.

In a preferred embodiment of the present invention, the above-mentioned photoelectric conversion layer is an opaque or transparent semiconductive layer.

In a preferred embodiment of the present invention, the above-mentioned substrate is located between the photoelectric conversion layer and the driving electrode layer, and the substrate is a transparent plate.

In a preferred embodiment of the present invention, both the above-mentioned driving electrode layer and the photoelectric conversion layer are transparent conductive films (TCF).

In a preferred embodiment of the present invention, the above-mentioned driving electrode layer is a metal layer, and the central electrode is adapted to reflect the light detecting beam.

In a preferred embodiment of the present invention, the above-mentioned photoelectrical device further includes a circuit substrate. The photoelectric conversion layer is formed on the circuit substrate, and the central electrode reflects the light detecting beam to the photoelectric conversion layer.

In a preferred embodiment of the present invention, the above-mentioned photoelectrical device further includes a transparent cover. The transparent cover is disposed oppositely to the substrate, wherein the driving electrode layer faces the transparent cover, and a detecting space is formed between the central electrode and the transparent cover.

In a preferred embodiment of the present invention, the above-mentioned photoelectrical device further includes a transparent electrode layer formed on the transparent cover, wherein the transparent electrode layer and the driving electrode layer face each other, and the transparent electrode layer is electrically connected to the AC power source.

In a preferred embodiment of the present invention, the above-mentioned peripheral electrode pattern includes a first ring electrode and a second ring electrode. The first ring electrode surrounds the central electrode by using the central electrode as the center. The second ring electrode surrounds the central electrode and the first ring electrode by using the central electrode as the center, wherein the first ring electrode and the second ring electrode are interdigiated and do not contact.

In a preferred embodiment of the present invention, the above-mentioned peripheral electrode pattern includes a ring electrode and a plurality of auxiliary electrodes. The ring electrode surrounds the central electrode by using the central electrode as the center. The auxiliary electrodes are connected with the ring electrode and extend radially from the ring electrode.

A method for concentration detection provided by the present invention includes the following steps of: performing an AC electrokinetic concentration (ACEK concentration) to gather up a plurality of target bioparticles in a fluid sample on a central electrode to form a particle cluster on the central electrode; thereafter, irradiating a light detecting beam at the particle cluster located on the central electrode; thereafter, using a photoelectric conversion layer to receive the light detecting beam (focused beam or focused light source is not required) that has passed through the particle cluster; thereafter, generating an magnitude of electric current by the photoelectric conversion layer based on an optical density of the light detecting beam; and finally, obtaining a concentration of the target bioparticles based on difference in electric current density compared to buffer only.

In a preferred embodiment of the present invention, the above-mentioned step of obtaining the concentration of the target bioparticles includes calculating a change rate of electric current based on the electric current and a background electric current, wherein the change rate of electric current is defined as the following mathematical formula:

$$\Delta I = [(Ib-Ic)/Ib] \times 100\%$$

wherein $\Delta I$ is the change rate of electric current, $Ib$ is the background electric current (buffer only), and $Ic$ is the electric current of bacteria (bacteria in buffer).

In a preferred embodiment of the present invention, the above-mentioned step of obtaining the concentration of the target bioparticles further includes comparing the change rate of electric current with a data look-up table to obtain a logarithmic value of the concentration of the target bioparticles.

In a preferred embodiment of the present invention, the above-mentioned change rate of electric current is positively correlated with the logarithmic value of the concentration of the target bioparticles.

In a preferred embodiment of the present invention, the above-mentioned data look-up table is obtained by logarithmic linear regression.

In a preferred embodiment of the present invention, the step of performing the AC electrokinetic concentration further includes using a dielectrophoresis (DEP) to drive a plurality of interfering (non-target) bioparticles in the fluid sample to move towards a direction away from the central electrode.

Based on the above, the photoelectrical device of the present invention can gather up the plurality of target bioparticles on the central electrode to concentrate the target bioparticles at one place. In this way, the photoelectrical device of the present invention can detect samples having a concentration of below $10^8$ CFU/ml without the need for long-term incubation (e.g., bacterial incubation). Thus, the photoelectrical device of the present invention can substantially shorten the incubation time much more than the conventional optical analysis instruments, and quickly detect the concentration of bioparticles at an early stage and the slight change rate of bacteria concentration thereof can be detected in only a short incubation time.

The structural features and the technical means adopted by the present invention to achieve the above and other objects can be best understood by referring to the following detailed description of the preferred embodiments and the accompanying drawings. However, the detailed description and the accompanying drawings are only used to explain and illustrate the present invention rather than as limitative of the appended claims of the present invention.

BRIEF DESCRIPTION OF THE DRAWINGS

The present invention will become more readily apparent to those ordinarily skilled in the art after reviewing the following detailed description and accompanying drawings, in which.

DETAILED DESCRIPTION OF PREFERRED EMBODIMENTS

Hereinafter, the present invention will be described in detail with drawings illustrating various embodiments of the present invention. However, the concept of the present invention may be embodied in many different forms and should not be construed as limitative of the exemplary embodiments set forth herein.

Figure 1A:
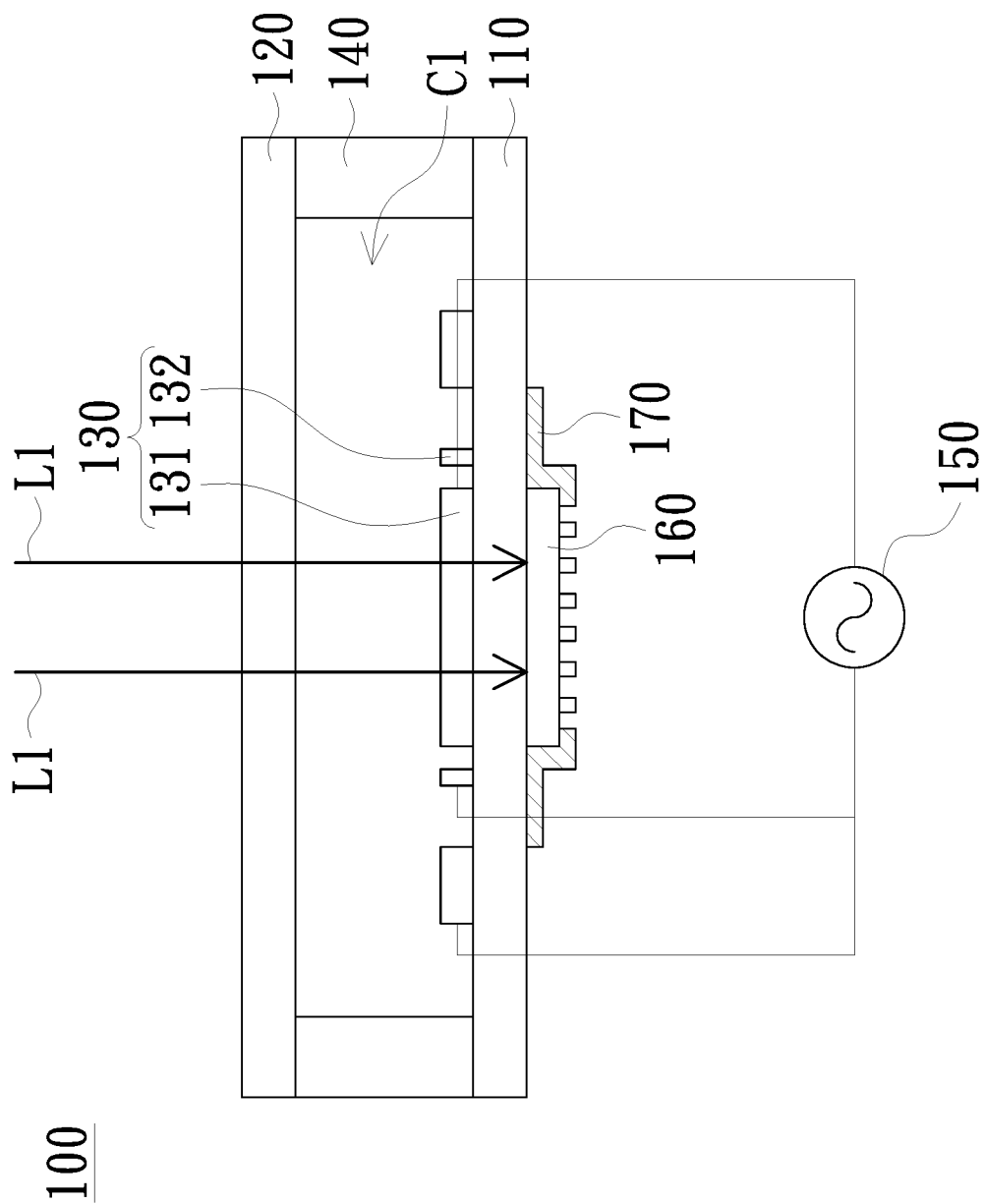
FIG. 1A is a schematic cross-sectional view of a photoelectrical device according to a preferred embodiment of the present invention.

Please refer to FIG. 1A, which is a schematic cross-sectional view of a photoelectrical device 100 according to a preferred embodiment of the present invention. The photoelectrical device 100 of the present invention can be used for detecting a concentration of bioparticles in a fluid sample, wherein the fluid sample can be a purified sample or an unpurified mixture sample, such as blood, urine, lactogenesis (e.g., milk) and perspiration. The bioparticles that can be detected by the photoelectrical device 100 include cells, microorganisms or biomolecules, wherein the microorganisms include viruses, Rickettsia, bacteria, fungi, molds and protists, and the protists can be planktons, algae, or single cell organisms such as amoeba. Biomolecules may include proteins as well as nucleic acids, wherein the proteins can be calibrated with or without fluorescence. In addition, the photoelectrical device 100 of the present invention may also be applied to food inspection and water quality detection. For examples, the photoelectrical device 100 may be used to detect the concentration of bacteria in an aquaculture pond, or to detect the concentration of bacteria in drinking water or milk.

The photoelectrical device 100 includes a substrate 110 and a transparent cover 120. The transparent cover 120 is disposed oppositely to the substrate 110, and a detecting space C1 is formed between the transparent cover 120 and the substrate 110, wherein a fluid sample to be detected can be placed in the detecting space C1. The photoelectrical device 100 can include a spacer 140, and the spacer 140 and the substrate 110 can form a detection groove having the detecting space C1, wherein the spacer 140 can surround a periphery of a asymmetrical concentric concentrated electrode group and be connected to the substrate 110. In addition, the shape of the spacer 140 can be a circular frame or a rectangular frame to surround the entire detecting space C1.

The substrate 110 can be a transparent plate, such as a glass plate or an acrylic plate, and the transparent cover 120 can be the aforementioned transparent plate. Therefore, both the substrate 110 and the transparent cover 120 are transparent, so that light, such as a light detecting beam L1, can penetrate the substrate 110 and the transparent cover 120. The light detecting beam L1 can be emitted from a pulsed light source (such as a laser) or a non-pulsed light source, and the wavelength range of the light detecting beam L1 can be between infrared light and ultraviolet light. It can be known that the substrate 110 can be located on the path of the light detecting beam L1 so that the light detecting beam L1 can penetrate the substrate 110 as shown in FIG. 1A. In addition, it should be explained that in the embodiment of FIG. 1A, the photoelectrical device 100 includes the transparent cover 120, but in other embodiments, the photoelectrical device 100 may not include the transparent cover 120 so that the light detecting beam L1 is directly irradiated at the fluid sample in the detecting space C1. Therefore, the transparent cover 120 shown in FIG. 1A is for illustrative purpose only, and does not limit the present invention.

The photoelectrical device 100 further includes a driving electrode layer 130 that is a transparent conductive film. The constituent material of the transparent conductive film can be a transparent conductive oxide (TCO), such as an indium tin oxide (ITO) or an indium zinc oxide (IZO). In addition, the constituent material of the above-mentioned transparent conductive film can be a conductive polymer, a nano metal wire, a carbon nanotube or graphene. Therefore, the driving electrode layer 130 can be made not only of a transparent conductive oxide, but also of a conductive polymer, a nano metal wire, a carbon nanotube or graphene. The driving electrode layer 130 is disposed on the substrate 110 and faces the transparent cover 120. The driving electrode layer 130 includes a central electrode 131, and the detecting space C1 is formed on the central electrode 131, wherein the fluid sample can be disposed on the driving electrode layer 130.

The photoelectrical device 100 of the present invention can perform an ACEK concentration in order that the driving electrode layer 130 gathers up the plurality of bioparticles at one place and separates different bioparticles, wherein the driving electrode layer 130 can use an inner electrode unit, an outer electrode unit, an auxiliary electrode unit and a bottom electrode disclosed in the U.S. patent with publication number U.S. Pat. No. 9,498,784B2, and the above-mentioned electrode units are drawn and shown in FIGS. 1, 4, 11(b), 11(c) and 11(d) of the U.S. patent with publication number U.S. Pat. No. 9,498,784B2.

Figure 1B:
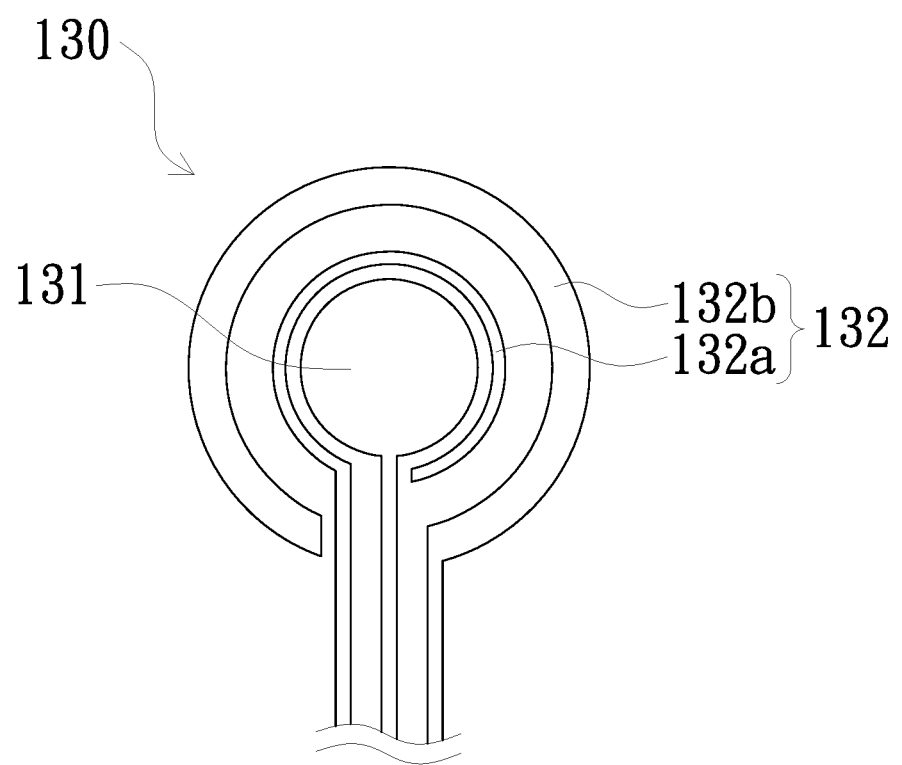
FIG. 1B is a wiring diagram of a driving electrode layer in FIG. 1A.

FIG. 1B is a wiring diagram of the driving electrode layer 130 in FIG. 1A, wherein the driving electrode layer 130 shown in FIG. 1B is drawn with reference to FIG. 1 of the U.S. patent with publication number U.S. Pat. No. 9,498,784B2. Please refer to FIGS. 1A and 1B, the driving electrode layer 130 further includes a peripheral electrode pattern 132. The peripheral electrode pattern 132 is located around the central electrode 131 but does not contact the central electrode 131. In order words, both the peripheral electrode pattern 132 and the central electrode 131 are electrically insulated from each other.

In the embodiment shown in FIG. 1B, the shape of the peripheral electrode pattern 132 is substantially concentric. Specifically, the peripheral electrode pattern 132 includes a first ring electrode 132a and a second ring electrode 132b. Both the first ring electrode 132a and the second ring electrode 132b surround the central electrode 131 by using the central electrode 131 as the center, and the second ring electrode 132b further surrounds the central electrode 131 and the first ring electrode 132a. In addition, the first ring electrode 132a and the second ring electrode 132b are not in contact with each other, that is, the first ring electrode 132a and the second ring electrode 132b are electrically insulated from each other.

Figure 1C:
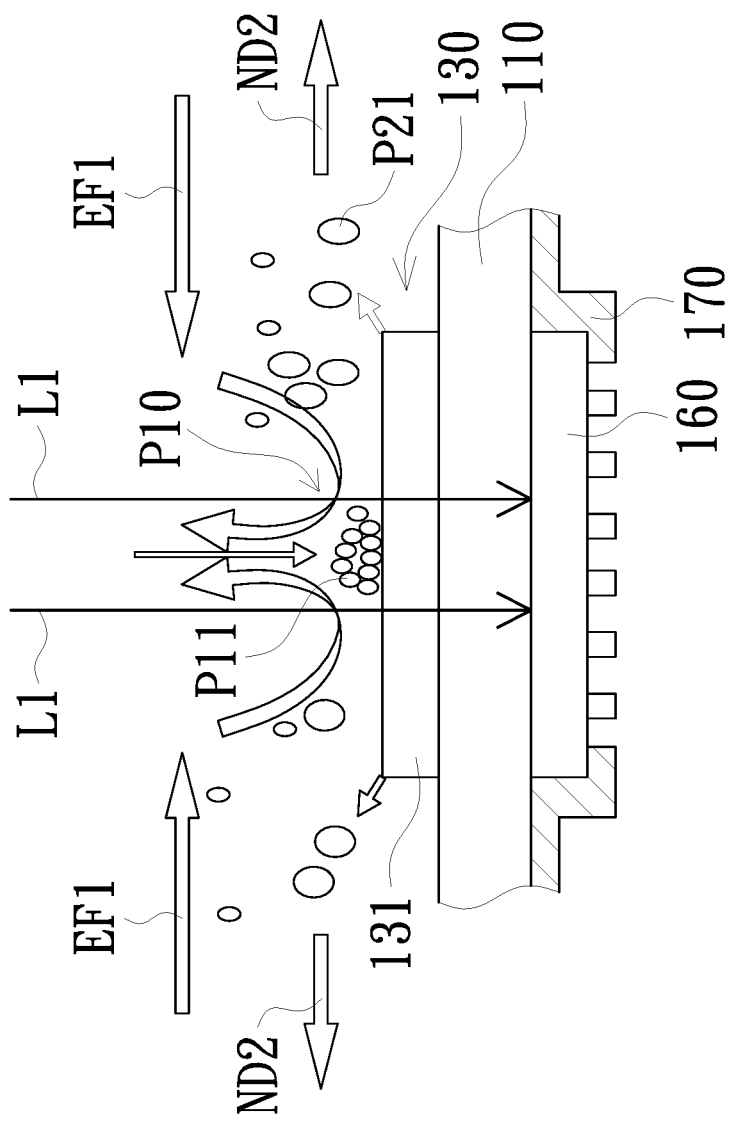
FIG. 1C is a schematic diagram of performing an AC electrokinetic concentration by the photoelectrical device in FIG. 1A.

FIG. 1C illustrates the mechanism of how the photoelectrical device 100 gathers up the bioparticles at one place and separates different bioparticles, which is the same mechanism disclosed in the U.S. patent with publication number U.S. Pat. No. 9,498,784B2. Specifically, please refer to FIGS. 1A and 1C. The photoelectrical device 100 further includes an AC power source 150, which can be a multi-output function generator and can output alternating currents with 0.1 volts to 20 volts and 0.1 Hz to 15 MHz. The AC power source 150 is electrically connected to the driving electrode layer 130. When the fluid sample is disposed on the driving electrode layer 130, the AC power source 150 can input an alternating current to the driving electrode layer 130 for generating a non-uniform alternating electric field inside the fluid sample on the driving electrode layer 130, which can drive a plurality of target bioparticles P11 to be gathered up on the central electrode 131 to form a particle cluster P10.

Specifically, the AC power source 150 is electrically connected to the central electrode 131, the first ring electrode 132a and the second ring electrode 132b of the driving electrode layer 130 (please refer to FIG. 1B). Since the central electrode 131, the first ring electrode 132a and the second ring electrode 132b are not in contact with each other, the three are electrically insulated from each other.

When the AC power source 150 outputs an alternating current to the driving electrode layer 130, the surfaces of the central electrode 131, the first ring electrode 132a and the second ring electrode 132b adsorb ions in the fluid sample, consequently the surface of the driving electrode layer 130 form an electrical double layer (EDL) by absorbing ions that are electrically different from each other, thereby generating an electric field that drives the ions. A large number of ions move in the fluid according to the electric field effect to generate an electrohydrodynamic force (EHD force), and thus the phenomenon of AC electroosmosis (ACEO) EF1 appears in the fluid.

The AC power source 150 can output an alternating current containing a DC bias to the driving electrode layer 130 so that the driving electrode layer 130 generates an asymmetric polarization to induce a wider range convection, thereby driving a plurality of bioparticles (including the target bioparticles P11) to migrate. The non-uniform alternating electric field generated by the driving electrode layer 130 can cause the AC electroosmosis EF1 to generate a net lateral flow that flows toward the central electrode 131 to migrate the fluid in a wide range, thereby gathering up the target bioparticles P11 at a fluid stagnation point/zone of the central electrode 131 as shown in FIG. 1C.

In addition, under the effect of the non-uniform alternating electric field generated by the driving electrode layer 130, dielectric particles, e.g., interfering bioparticles P21, in the fluid sample generate dielectrophoresis (DEP). If the dielectric particles are more easily polarizable than the surrounding medium, the dielectric particles will be attracted by the strong electric field to produce a positive DEP (pDEP). Contrarily, if the dielectric particles are less easily polarizable than the surrounding medium, the dielectric particles will be attracted by the weak electric field to produce a negative DEP (nDEP). The degree of polarization of both the dielectric particles and the surrounding medium can be changed by changing the frequency of the alternating current. Therefore, by adjusting the frequency of the alternating current output by the AC power source 150, the dielectric particles can be controlled to produce a positive or negative dielectrophoresis.

Whether a positive dielectrophoresis or a negative dielectrophoresis, the intensity of both are directly proportional to a volume of the dielectric particles, that is, directly proportional to the third power of the particle diameter of the dielectric particles. In this embodiment, both the particle diameter and volume of the interfering bioparticles P21 are larger than that of the target bioparticles P11. Therefore, by the AC power source 150 outputting an alternating current with an appropriate frequency to the driving electrode layer 130, the interfering bioparticles P21 can generate a negative dielectrophoresis ND2 with sufficient resistance to the AC electroosmosis EF1.

By using the negative dielectrophoresis ND2, the driving electrode layer 130 can drive the interfering bioparticles P21 in the fluid sample to move towards a weak electric field, wherein the weak electric field is mostly formed at the periphery of the driving electrode layer 130, and therefore the dielectrophoresis ND2 will make the interfering bioparticles P21 move towards a direction away from the central electrode 131. Contrarily, by using the AC electroosmosis with positive DEP (not shown in FIG. 1C), the driving electrode layer 130 can drive the target bioparticles P11 in the fluid sample to move towards a strong electric field, wherein the strong electric field and the fluid stagnation point are mostly formed at the central electrode 131, and therefore the positive dielectrophoresis will make the target bioparticles P11 move in a direction towards the central electrode 131. In this way, the interfering bioparticles P21 and the target bioparticles P11 move in the opposite directions, thereby separating the interfering bioparticles P21 and the target bioparticles P11. In other words, the photoelectrical device 100 not only can detect purified samples, but can also detect unpurified mixture samples such as blood, urine, ascites or lactogenesis.

In order to enable the dielectrophoresis ND2 that drives the interfering bioparticles P21 to resist the AC electroosmosis EF1 so that the interfering bioparticles P21 can smoothly move away from the central electrode 131, an average particle diameter of the interfering bioparticles P21 is not only larger than an average particle diameter of the target bioparticles P11, and a ratio of the average particle diameters of both (interfering bioparticles P21:target bioparticles P11) needs to be limited. Specifically, under the condition that the average particle diameters of both the interfering bioparticles P21 and the target bioparticles P11 are on the micron-scale level, the ratio of the average particle diameters of the interfering bioparticles P21 to the target bioparticles P11 needs to be greater than or equal to 1.5. Under the condition that the average particle diameters of both the interfering bioparticles P21 and the target bioparticles P11 are on the nano-scale level, the ratio of the average particle diameters of the interfering bioparticles P21 to the target bioparticles P11 needs to be greater than or equal to 10.

Since the AC power source 150 can use the driving electrode layer 130 to separate the interfering bioparticles P21 and the target bioparticles P11 and gather up most or all of the target bioparticles P11 on the central electrode 131 to form the particle cluster P10, the central electrode 131 has significant light absorption and scattering properties due to the occupation of the particle cluster P10. For example, the central electrode 131 will display a turbid appearance. At this time, the photoelectrical device 100 can detect the concentration of the target bioparticles P11 through the light detecting beam L1. Particularly, the photoelectrical device 100 can detect the concentration of the target bioparticles P11 by sensing the transmittance of the particle cluster P10 for the light detecting beam L1. In a preferred embodiment of the present invention, the photoelectrical device 100 senses the above-mentioned transmittance by using the photoelectric effect.

Specifically, the photoelectrical device 100 further includes a photoelectric conversion layer 160 and senses the transmittance of the particle cluster P10 by using the photoelectric effect generated by the photoelectric conversion layer 160. Since the photoelectric conversion layer 160 is disposed on the substrate 110 and is opposite to the driving electrode layer 130, the substrate 110 is located between the photoelectric conversion layer 160 and the driving electrode layer 130. Both the central electrode 131 and the photoelectric conversion layer 160 are located on the path of the light detecting beam L1. Therefore, the light detecting beam L1 can pass through the central electrode 131 and the substrate 110 sequentially and then enter the photoelectric conversion layer 160.

When the particle cluster P10 is formed on the central electrode 131, the photoelectric conversion layer 160 can receive the light detecting beam L1 after passing through the particle cluster P10. Since the photoelectric conversion layer 160 has a photoelectric effect characteristic, the photoelectric conversion layer 160 can output an electric current according to the illuminance of the light detecting beam L1 after the photoelectric conversion layer 160 has received the light detecting beam L1, wherein the magnitude of the electric current is directly proportional to the intensity of the light detecting beam L1 received by the photoelectric conversion layer 160. In other words, the higher the transmittance of the particle cluster P10 for the light detecting beam L1, the larger the electric current output by the photoelectric conversion layer 160. Contrarily, the lower the transmittance of the particle cluster P10 for the light detecting beam L1, the smaller the electric current output by the photoelectric conversion layer 160.

The transmittance of the particle cluster P10 is related to the concentration of the target bioparticles P11. Specifically, the higher the concentration of the target bioparticles P11, the denser the particle cluster P10, so that the lower the transmittance, the smaller the electric current output by the photoelectric conversion layer 160. On the contrary, the lower the concentration of the target bioparticles P11, the more sparse the particle group P10 is, so that the higher the transmittance, and the larger the electric current output by the photoelectric conversion layer 160. From this, it can be known that the electric current output by the photoelectric conversion layer 160 changes as the concentration of the target bioparticles P11 changes. It can be known that, the photoelectrical device 100 can detect the concentration of the target bioparticles P11 by measuring the electric current output by the photoelectric conversion layer 160.

Figure 1D:
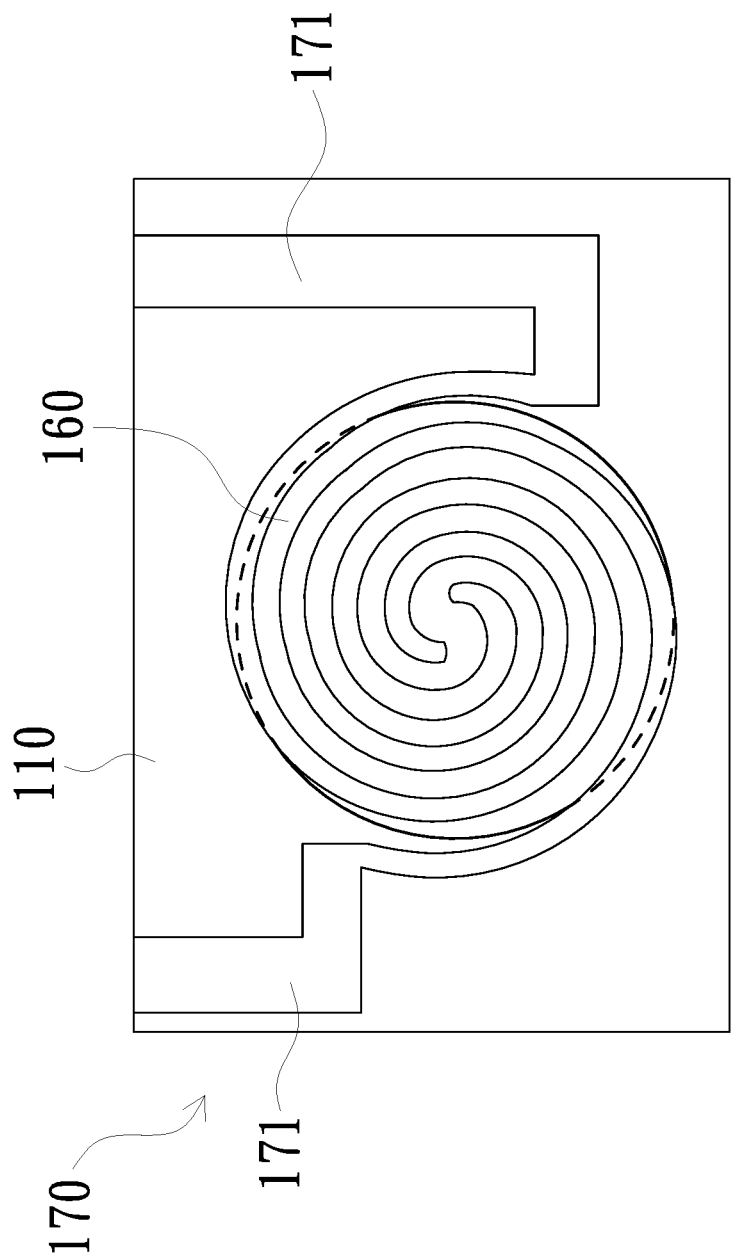
FIG. 1D is a wiring diagram of a measurement electrode pattern and a photoelectric conversion layer in FIG. 1A.

FIG. 1D is a wiring diagram of the measurement electrode pattern 170 and the photoelectric conversion layer 160 in FIG. 1A. Please refer to FIGS. 1A and 1D, the photoelectrical device 100 can further include the measurement electrode pattern 170. The measurement electrode pattern 170 is connected to the photoelectric conversion layer 160 and can transmit the electric current output by the photoelectric conversion layer 160. The measurement electrode pattern 170 includes a pair of measurement electrodes 171 that do not contact with each other, and the measurement electrodes 171 have a spiral shape as shown in FIG. 1D, or can be a graphic in a finger-intersecting shape, a spiral finger-intersecting shape, or a radial finger-intersecting shape. In this embodiment, the material of the measurement electrodes 171 can include metals, such as platinum or aurum with good electric conductivity, and the material of the photoelectric conversion layer 160 can include metal oxides with photoelectric characteristics, such as zinc oxide (ZnO). Therefore, the photoelectric conversion layer 160 can be a transparent conductive film. However, in other embodiments, the material of the photoelectric conversion layer 160 can also include silicon, such as amorphous silicon and polycrystalline silicon, and therefore the photoelectric conversion layer 160 can also be a translucent layer or an opaque layer.

Figure 2A:
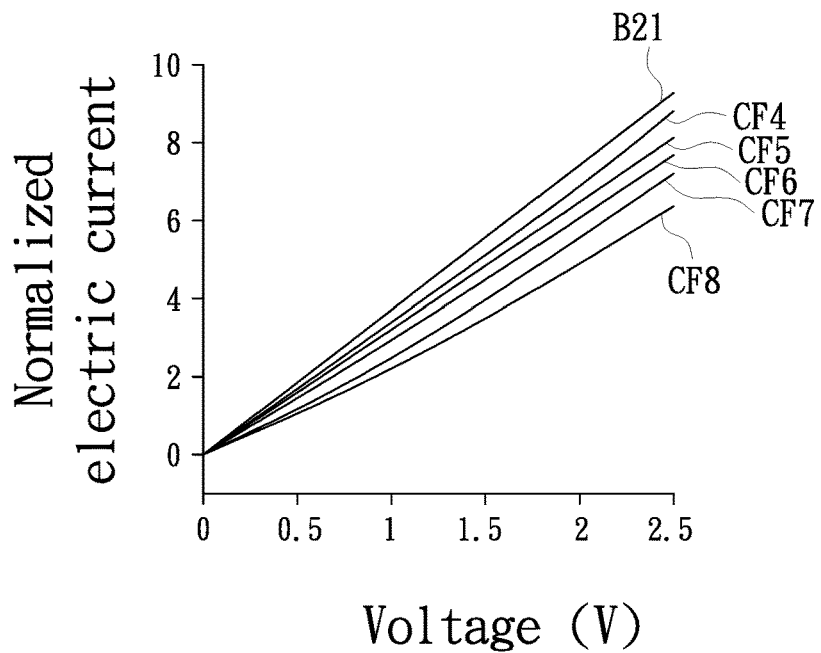
FIG. 2A is an electric current-voltage curve (I-V curve) obtained by detecting samples of different concentrations with the photoelectrical device of the present invention.

FIG. 2A is an electric current-voltage curve obtained by detecting samples of different concentrations with the photoelectrical device of the present invention, wherein the vertical axis represents the electric currents output by the photoelectric conversion layer 160 according to the received light detecting beam L1, and the horizontal axis represents the voltages input to the photoelectric conversion layer 160. In addition, the electric currents shown on the vertical axis are normalized results, and therefore the numerical values on the vertical axis are not the actual electric currents.

FIG. 2A depicts a plurality of curves B21 and CF4 to CF8, and these curves B21 and CF4 to CF8 are drawn by measuring a plurality of fluid samples of different concentrations. In detail, the curve B21 is background information and is drawn by detecting a sterile fluid sample, wherein the sterile fluid sample can be an isotonic phosphate buffered saline (PBS), which can be doped with mannitol and can act as a buffer. The electric conductivity of the above-mentioned sterile fluid sample can be controlled at about 1 to 500 µS/cm for facilitating the generation of the AC electroosmosis and dielectrophoresis (as shown in FIG. 1C), wherein the AC electroosmosis with positive DEP is used to gather up the bacteria on the central electrode 131. The curves CF4 to CF8 are sequentially obtained by detecting fluid samples with bacterial concentrations of $6 \times 10^4$ CFU/ml, $3 \times 10^5$ CFU/ml, $3 \times 10^6$ CFU/ml, $3 \times 10^7$ CFU/ml and $3 \times 10^8$ CFU/ml, wherein the fluid samples are made by adding bacteria to the above-mentioned sterile fluid sample.

The curve B21 and CF4 to CF8 are detected and drawn with the photoelectrical device 100 under the following conditions. The photoelectrical device 100 uses an ultraviolet light having an intensity of about 1 mW/cm$^2$ and a wavelength of between 350 nm and 400 nm as the light detecting beam L1, which is irradiated at the above-mentioned fluid samples (including the sterile fluid sample). It is understood that the light detecting beam L1 of other wavelengths can also be used depending on the photoelectric conversion layer 160 of different materials. The AC power source 150 supplies a 10 Vpp alternating current to the second ring electrode 132b, supplies a 6 Vpp alternating current to the first ring electrode 132a, and supplies a 0.5 V DC bias to the center electrode 131 to generate a non-uniform electric field, wherein an alternating current frequency provided by the AC power source 150 to the first ring electrode 132a and the second ring electrode 132b can be about 3 kHz. In addition, all the fluid samples are detected for concentration after 8 minutes of AC electrokinetic concentration.

As seen from FIG. 2A, the slopes of the curve B21 and CF4 to CF8 are related to the concentration, wherein the larger the slope (more steep), the lower the concentration of the target bioparticles P11. On the contrary, the smaller the slope (more gradual), the higher the concentration of the target bioparticles P11. Additionally, the change rates of electric current between the individual curves CF4 to CF8 and the curve B21 are also related to the concentration, as shown in FIG. 2B.

Figure 2B:
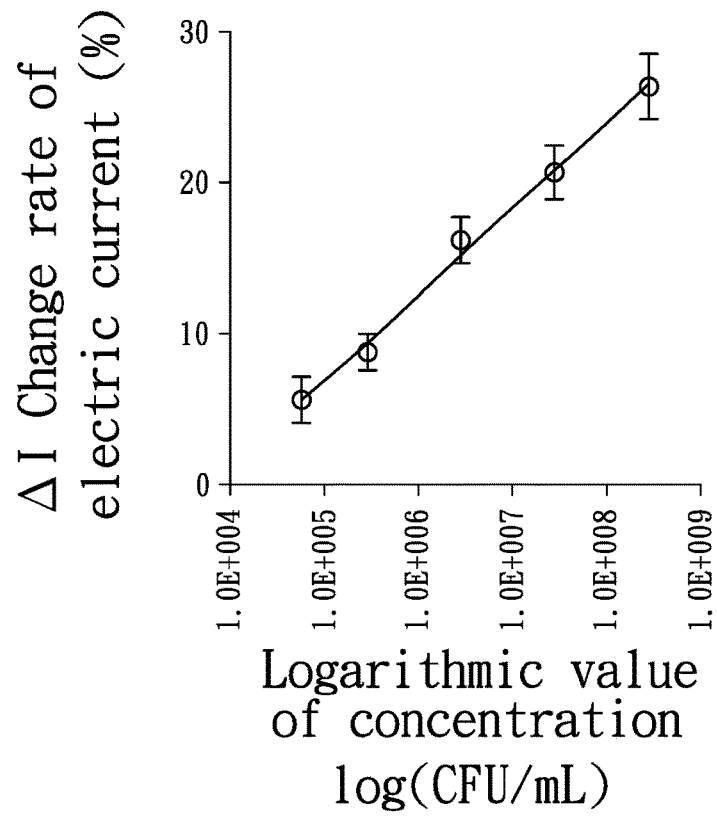
FIG. 2B is a graph illustrating the relationship between a change rate of electric current and a logarithmic value of concentration plotted according to FIG. 2A.

FIG. 2B is a graph illustrating the relationship between the change rate of electric current and the logarithmic value of concentration plotted according to FIG. 2A. Please refer to FIG. 2B. In FIG. 2B, the vertical axis represents the change rates of electric current, and the horizontal axis represents the logarithmic values of concentration of the fluid samples, wherein the change rate of electric current is defined as shown in the following mathematical formula (1).

$$\Delta I = [(Ib-Ic)/Ib] \times 100\% \qquad (1)$$

$\Delta I$ is the change rate of electric current, Ib is the background electric current, and Ic is the electric current measured by detecting the bacteria-containing fluid samples. The background electric current Ib is, for example, the electric current obtained by detecting the above-mentioned sterile fluid sample (i.e., the isotonic phosphate buffered saline corresponding to the curve B21), and the electric current Ic is the electric current obtained by detecting the fluid samples corresponding to the curves CF4 to CF8 individually. Therefore, the electric current Ib−Ic contains information on the concentration of bacteria.

The circular patterns indicated in FIG. 2B represent the change rates of electric current of the curves CF4 to CF8 from left to right respectively, wherein the bottom left circular pattern is the change rate of electric current of the curve CF4, that is, the detection result of the fluid sample with the bacterial concentration of $6\times10^4$ CFU/ml, its change rate of electric current is 5.82±1.47%. This change rate of electric current of this magnitude is sufficient to discriminate the information (curve CF4) of the bacteria-containing fluid sample ($6\times10^4$ CFU/ml) and the background information (curve B21). However, for fluid samples with a bacterial concentration below $6\times10^4$ CFU/ml, for example $3\times10^4$ CFU/ml, the detected change rate of electric current will be less than 3%, and therefore it is difficult to distinguish between the information of the fluid samples with bacterial concentration lower than $6\times10^4$ CFU/ml and the background information. Therefore, the photoelectrical device 100 having a local bacterial enrichment function can detect a concentration range of approximately above $6\times10^4$ CFU/ml. Compared with the conventional optical analysis instruments, the photoelectrical device 100 of the present invention can detect fluid samples having a bioparticle concentration of below $10^8$ CFU/ml, thus having a relatively lower concentration detection limit and is also capable of detecting a wider range of bioparticle concentrations.

In addition, it can also be seen from FIG. 2B that the change rate of electric current and the logarithmic value of the concentration of the target bioparticles P11 are positively correlated, and therefore linear regression can be used to obtain the data look-up table, as shown by the oblique line in FIG. 2B. Through this data look-up table, the photoelectrical device 100 can calculate the concentration of the target bioparticles P11 based on the electric current obtained by the photoelectric conversion layer 160 detecting the fluid samples.

Figure 2C:
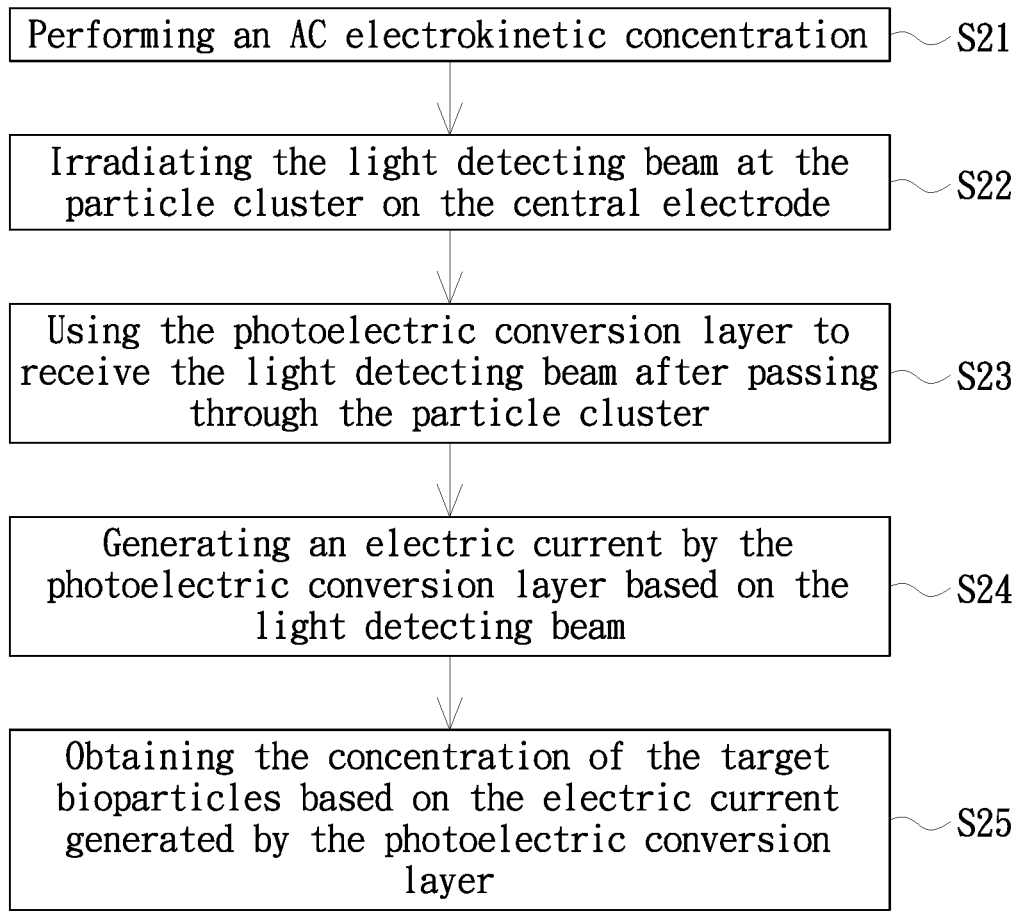
FIG. 2C is a schematic flowchart of a method for concentration detection according to a preferred embodiment of the present invention.

FIG. 2C is a schematic flowchart of a method for concentration detection according to a preferred embodiment of the present invention. Please refer to FIGS. 1A, 1C and 2C. According to the data look-up table obtained in FIG. 2B (i.e., the oblique line shown in FIG. 2B), the photoelectrical device 100 of the present invention can detect the concentration of the target bioparticles P11, for example, the concentration of bacteria in blood, wherein the method for concentration detection is as follows.

Firstly, after disposing the fluid sample on the driving electrode layer 130 in the detecting space C1, step S21 is performed to carry out the AC electrokinetic concentration to gather up the plurality of target bioparticles P11 in the fluid sample on the central electrode 131 so as to form the particle cluster P10 on the central electrode 131, wherein the target bioparticles P11 are, for example, bacteria, and the AC electrokinetic concentration can be performed for a period of between 1 and 30 minutes, for examples 5 minutes or 8 minutes. During the process of the AC electrokinetic concentration, the plurality of interfering bioparticles P21 in the fluid sample, such as blood cells, can be driven by a negative dielectrophoresis (nDEP) to move towards a direction away from the central electrode 131. In this way, the interfering bioparticles P21 (e.g., blood cells) will not flow to the central electrode 131, thereby separating the target bioparticles P11 (e.g., bacteria) and the interfering bioparticles P21 (e.g., blood cells).

Step S22 is performed to irradiate the light detecting beam L1 at the particle cluster P10 on the central electrode 131. Thereafter, step S23 is performed to use the photoelectric conversion layer 160 to receive the light detecting beam L1 that has passed through the particle cluster P10. Thereafter, step S24 is performed to configure the photoelectric conversion layer 160 to generate an electric current based on the light detecting beam L1. Finally, step S25 is performed to obtain the concentration of the target bioparticles P11 based on the electric current generated by the photoelectric conversion layer 160.

In the process of performing step S25, the change rate of electric current is calculated according to the electric current generated by the photoelectric conversion layer 160 and the background electric current (e.g., the aforementioned background electric current Ib), wherein the calculation method is as shown in the above-mentioned mathematical formula (1). After the change rate of electric current is calculated, the calculated change rate of electric current is compared with the data looked-up table (the oblique line as shown in FIG. 2B) and thereby obtaining the logarithmic value of the concentration of the target bioparticles P11. Thereafter, logarithmic operations are performed on the logarithmic value of the concentration, thereby calculating the concentration of the target bioparticles P11, such as the concentration of bacteria in liquid or blood. It can be known that, the photoelectrical device 100 can quantitatively analyze the concentration of the bioparticles (e.g., bacteria) by using the photoelectric conversion layer 160 to receive the electric current generated by the light detecting beam L1.

Figure 3A:
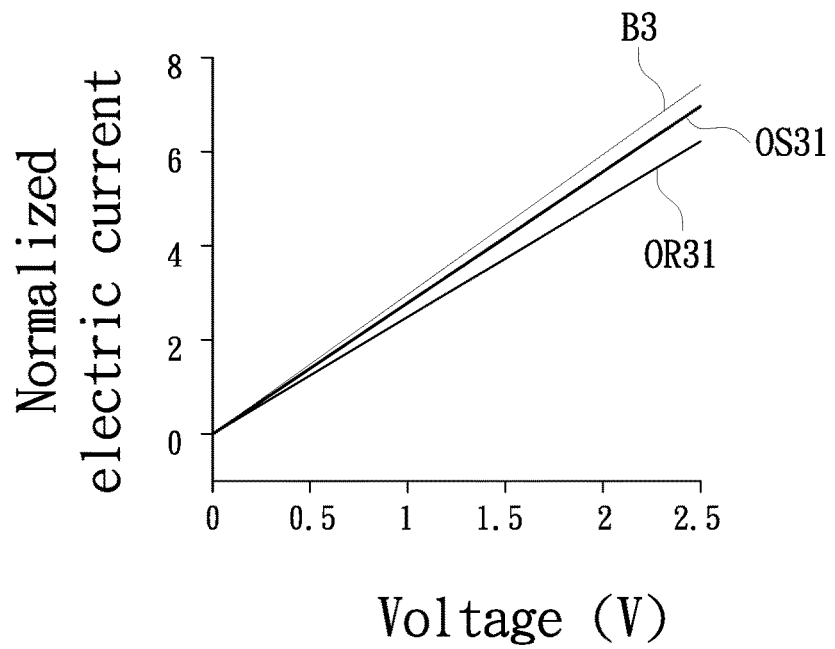
FIG. 3A is an electric current-voltage curve obtained by the photoelectrical device of the present invention for detecting an effectiveness of an antibiotic.
Figure 3B:
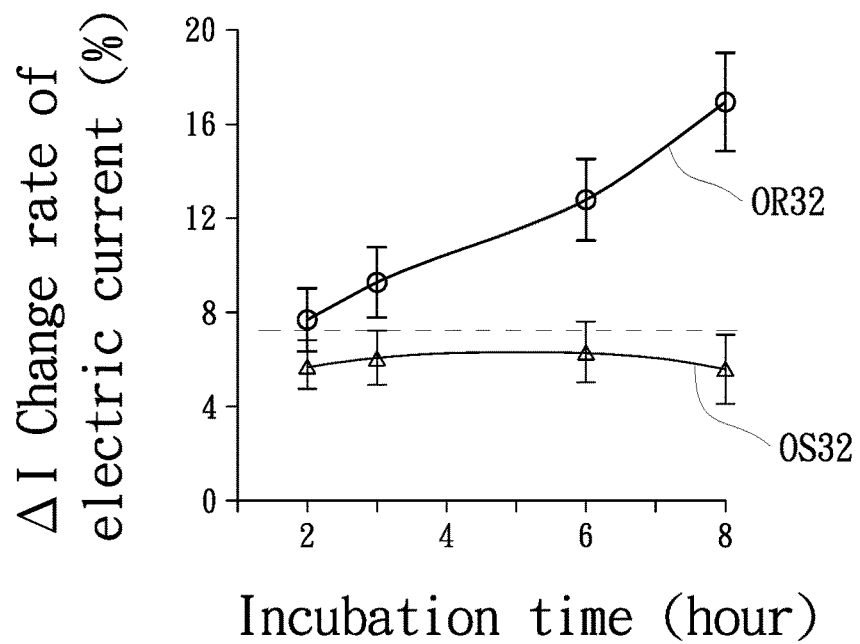
FIG. 3B is a diagram illustrating the relationship between the change rate of electric current and an incubation time plotted according to FIG. 3A.

It is worth mentioning that since the photoelectrical device 100 can quantitatively analyze the concentration of the bioparticles, and the photoelectrical device 100 can detect the fluid samples with low cell density and distinguish the fluid samples with low cell density differences, such as the fluid samples with concentration below $10^8$ CFU/ml and distinguish the concentration differences of $10^4$–$10^8$ CFU/ml, and can also separate the bioparticles (such as the separation of bacteria and blood cells), the photoelectrical device 100 is considerably suitable for using in a method for testing the effectiveness of antibiotics on bacteria, especially the detection of antibiotice and susceptibility of bacteria, as shown in FIGS. 3A and 3B. In addition, the effectiveness of antibiotics on bacteria described herein refers not only to antibiotice and susceptibility, but also to other meanings commonly used for inhibitory effect and applicability in different requirement situations.

FIG. 3A is an electric current-voltage curve obtained by the photoelectrical device of the present invention for detecting an effectiveness of an antibiotic on bacteria. In the method for testing the effectiveness of an antibiotic on bacteria of the present invention, firstly, a fluid sample containing bacteria and an antibiotic is prepared, wherein the bacterial concentration of the fluid sample is between $10^4$ and $10^5$ CFU/ml. Use FIG. 3A as an example, the fluid sample to be detected contains an antibiotic: oxacillin, and bacteria: oxacillin-resistant *Staphylococcus aureus* (ORSA, hereinafter as ORSA for short). There is also another control sample used as a control group containing oxacillin and oxacillin-susceptible *Staphylococcus aureus* (OSSA, hereinafter as OSSA for short). In FIG. 3A, curve B3 is the background information and is drawn by detecting a sterile fluid sample. Curve OS31 is drawn by detecting the control sample containing OSSA and oxacillin, and curve OR31 is drawn by detecting a fluid sample containing ORSA and oxacillin.

Both the above fluid sample and the control sample are added with oxacillin of a concentration of about 4 μg/ml in the tryptic soy broth (TSB) to incubate OSSA and ORSA respectively, and both of them respectively contain OSSA and ORSA with a bacterial concentration of $6\times10^4$ CFU/ml. After preparing the above fluid sample and the control sample, the bacteria (ORSA) in the fluid sample and the bacteria (OSSA) in the control sample are incubated, wherein the time for incubating the bacteria can be more than 3 hours, for example, 4 hours. After incubating the bacteria, steps S21 to S24 shown in FIG. 2C are sequentially performed.

Specifically, the AC electrokinetic concentration (step S21) is performed first to gather up the bacteria OSSA and ORSA in the fluid sample and the control sample on the central electrode 131 so as to form the particle cluster P10 on the central electrode 131, wherein the AC electrokinetic concentration is conducted for the fluid sample and the control sample in the different photoelectrical devices 100. Alternatively, the AC electrokinetic concentration is conducted for the fluid sample and the control sample sequentially and asynchronously in the same photoelectrical device 100.

Thereafter, the light detecting beam L1 is irradiated at the particle cluster P10 on the central electrode 131 (step S22), wherein the light detecting beam L1 is individually irradiated at the two different particle clusters P10 containing OSSA and ORSA. Thereafter, the photoelectric conversion layer 160 is used to receive the light detecting beam L1 that has passed through the particle cluster P10 (step S23). Based on the light detecting beam L1, the photoelectric conversion layer 160 generates an electric current (step S24), wherein there are two kinds of electric currents, one corresponding to the control sample containing the OSSA and the other corresponding to the fluid sample containing the ORSA. Based on these two electric currents, two different change rates of electric current are obtained, wherein the change rates of electric current are defined as shown in the above mathematical formula (1) and are illustrated in FIG. 3A. It can be clearly seen from FIG. 3A that the slope of the curve OR31 is significantly smaller than the slopes of the curves OS31 and B31. Obviously, the bacteria (ORSA) concentration of the curve OR31 is greater than the bacteria (OSSA) concentration of the curve OS31.

FIG. 3B is a diagram illustrating the relationship between the change rate of electric current and the incubation time measured on the photoelectric device 100 after being incubated for different periods of time based on FIG. 3A, wherein the vertical axis represents the change rate of electric current and its definition is the same as the above mathematical formula (1), while the horizontal axis represents the incubation time (also referred to as incubation period). Please refer to FIGS. 3A and 3B. The curve OR32 in FIG. 3B corresponds to the curve OR31 in FIG. 3A, and the curve OS32 in FIG. 3B corresponds to the curve OS31 in FIG. 3A. In other words, both the curves OR31 and OR32 correspond to the same fluid sample containing the ORSA, both the curves OS31 and OS32 correspond to the same control sample containing the OSSA, and the curve OS32 represents the change rate of electric current of the control group.

It can be clearly seen from FIG. 3B that after more than 3 hours of incubation period, the difference between the change rates of electric current of the ORSA fluid sample and the OSSA control sample is greater than or equal to a pre-determined criteria (e.g, 4%), so that there is a significant difference sufficient to reach the level of discrimination. Afterwards, as the incubation time (incubation period) increases, there is no significant change in the change rate of electric current of the OSSA fluid sample (curve OS32). This indicates that the OSSA is inhibited by oxacillin and difficult to reproduce. This result also indicates that the initial concentration of OSSA (reaction time 0 hour) can be used as a control group. Contrarily, there is a significant increase in the change rate of electric current of the ORSA fluid sample (curve OR32). Even after 4 hours of incubation time, the change rate of electric current of the ORSA fluid sample is more than 10% as shown in FIG. 3B. This means that the ORSA is not inhibited by oxacillin, so that the ORSA can still continue to reproduce.

It can be seen that when the difference between the change rates of electric current of the fluid sample to be measured (e.g., the curve OR32) and the control group (e.g., the curve OS32) is more than or equal to 4%, it can be determined that the antibiotic (e.g., oxacillin) has no effectiveness on the bacteria (e.g., ORSA). When the difference between the change rates of electric current of the fluid sample to be measured (e.g., the curve OR32) and the control group (e.g., the curve OS32) is less than 4%, it can be determined that the antibiotic (e.g., oxacillin) has an effectiveness on the bacteria (e.g., OSSA). In addition, the data of the change rate of electric current (e.g., the curve OS32) of the control group can be stored in an electronic device (e.g., a computer) and can be mathematically made into a database (e.g., the oblique line shown in FIG. 2B). Through this database, the photoelectrical device 100 can determine whether the antibiotic is effective based on the obtained change rate of electric current of the fluid sample. Therefore, the method of the present invention for testing the effectiveness of an antibiotic on bacteria can use computer software, and then, after testing the initial concentration of the sample (0 hour), directly test the sample after 3 hours of incubation with the antibiotic, and compare the difference to determine the antibiotic's effectiveness without the need of preparing the above OSSA control sample for the determination of the antibiotic's effectiveness.

Since the photoelectrical device 100 can detect the difference in bacterial growth rate between a liquid sample having a low bacterial concentration (e.g., $6\times10^4$ CFU/ml) and a short incubation time, the bacterial samples incubated for a short time (e.g., 3 or 4 hours) can be detected. Compared to the conventional optical analysis instruments, the present invention does not require bacterial incubation for a long period of time (more than one day) to rapidly perform quantitative analysis of the fluid samples and perform analysis of the effectiveness of an antibiotic based on differences in micro-bacterial density, such as antibiotice analysis and antibiotic susceptibility analysis. Alternatively, it can determine whether a certain antibiotic responds to a certain bacterium, for example, determine whether the antibiotic can inhibit the growth of bacteria or kill the bacteria, or evaluate the recovery of infection, or determine whether the antibiotic can promote the proliferation of bacteria (number of probiotics) beneficial to human body. In this way, the photoelectrical device 100 of the present invention can significantly shorten the incubation time (or bacterial growth time) required for detection, thereby effectively accelerating the detection of the concentration of bioparticles and the effectiveness analysis.

Figure 4A:
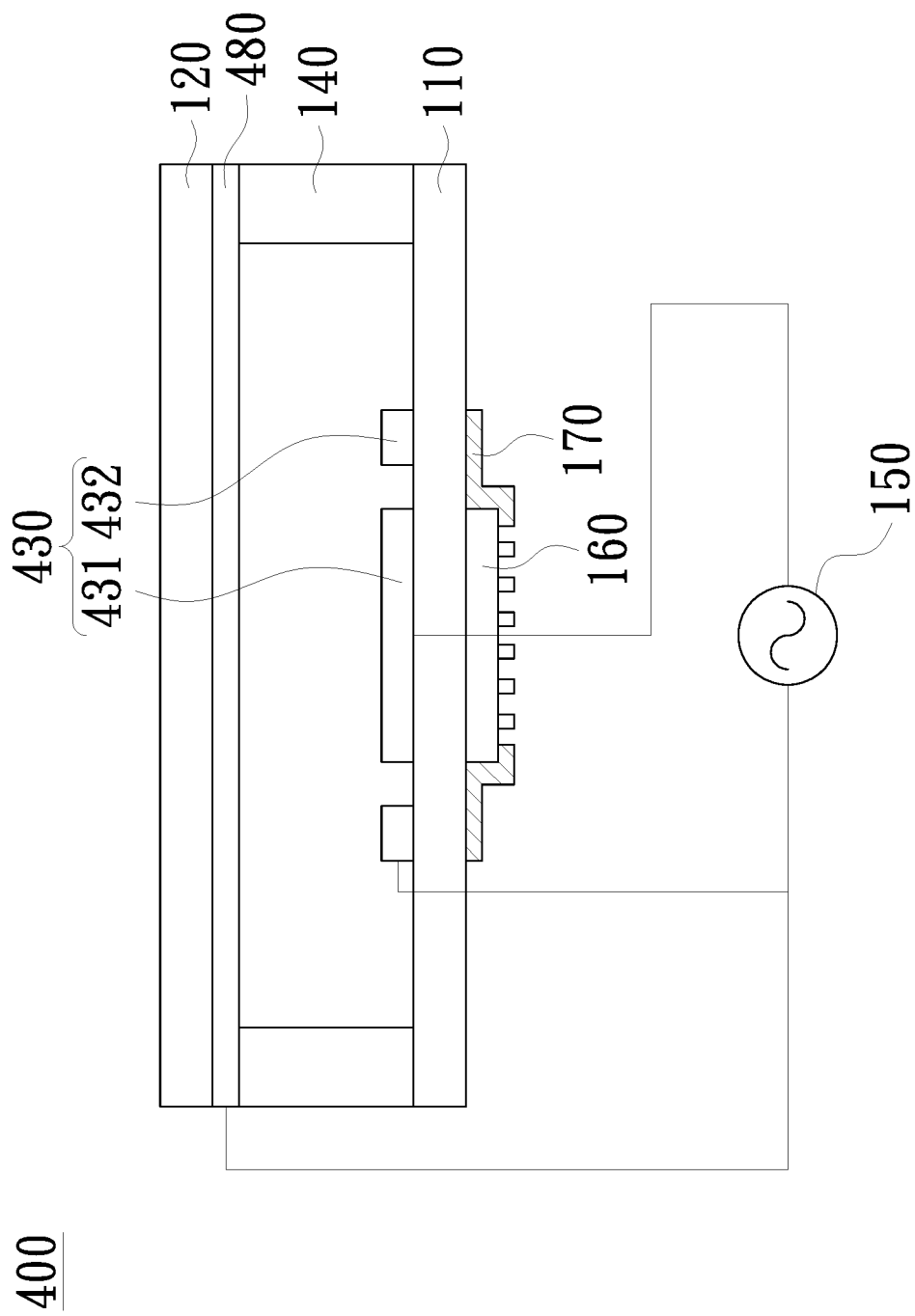
FIG. 4A is a schematic cross-sectional view of a photoelectrical device according to another preferred embodiment of the present invention.
Figure 4B:
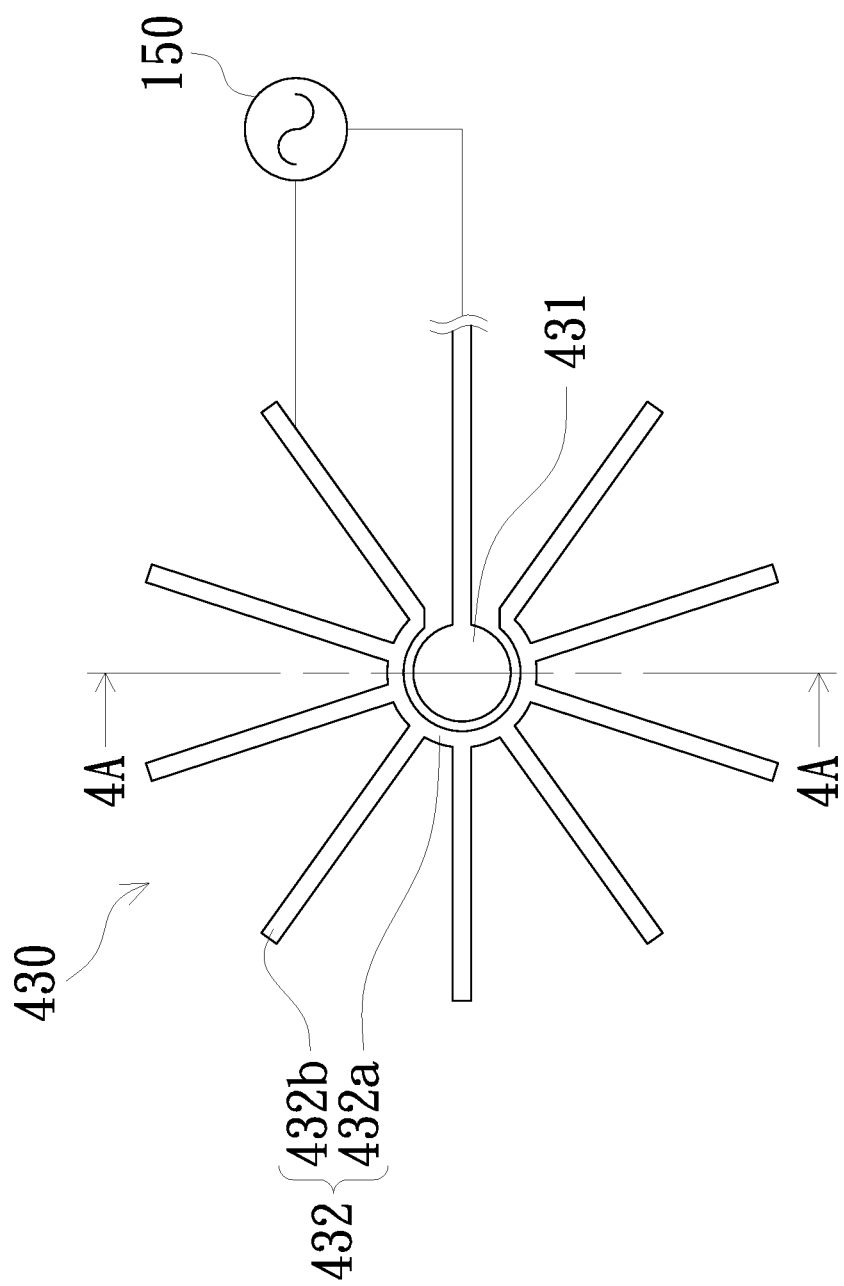
FIG. 4B is a wiring diagram of a driving electrode layer in FIG. 4A.

FIG. 4A is a schematic cross-sectional view of the photoelectrical device according to another preferred embodiment of the present invention, and FIG. 4B is a wiring diagram of a driving electrode layer 430 in FIG. 4A. Please refer to FIGS. 4A and 4B, a photoelectrical device 400 of this embodiment is similar to the photoelectrical device 100 shown in FIG. 1A. For example, both of the photoelectrical devices 100 and 400 also include the same elements, and the methods of both for the efficacy and concentration detection are the same. Therefore, only the differences between the photoelectrical devices 100 and 400 will be described below, and the similarities will not be described again.

In the photoelectrical device 400, the photoelectrical device 400 further includes a transparent electrode layer 480 formed on the transparent cover plate 120. The transparent electrode layer 480 and a driving electrode layer 430 face each other, and the transparent electrode layer 480 is electrically connected to the AC power source 150. When the AC power source 150 outputs a voltage to the transparent electrode layer 480, a non-uniform vertical electric field can be generated between the transparent electrode layer 480 and the driving electrode layer 430, which can also help to separate the target bioparticles P11 and the interfering bioparticles P21, and gather up the target bioparticles P11 (please refer to FIG. 1C).

The wiring pattern of the driving electrode layer 430 is shown in FIG. 4B, and is also disclosed in FIG. 11(c) of the U.S. patent with publication number U.S. Pat. No. 9,498,784B2. The driving electrode layer 430 includes a central electrode 431 and a peripheral electrode pattern 432. The shape of the central electrode 431 is roughly the same as that of the central electrode 131 shown in FIG. 1B, and the peripheral electrode pattern 432 includes a ring electrode 432a and a plurality of auxiliary electrodes 432b. The ring electrode 432a surrounds the central electrode 431 by using the central electrode 431 as the center. The auxiliary electrodes 432b are connected to the ring electrode 432a and extended radially from the ring electrode 432a. The peripheral electrode pattern 432 is not in contact with the central electrode 431, and therefore both the peripheral electrode pattern 432 and the central electrode 431 are electrically insulated from each other. In addition, the material of the driving electrode layer 430 can be the same as the material of the driving electrode layer 130 or can be replaced with an insulating material.

Since these auxiliary electrodes 432b extend radially from the ring electrode 432a, a distance between the two adjacent auxiliary electrodes 432b increases as a distance away from the ring electrode 432a increases. Therefore, an electric field generated between the two adjacent auxiliary electrodes 432b gradually decreases from the inside to the outside of the ring electrode 432a. Therefore, the two adjacent auxiliary electrodes 432b generate a strong electric field near the central electrode 431. On the contrary, a weak electric field is generated between the ends of two adjacent auxiliary electrodes 432b. In this way, the AC power source 150 can also generate a negative dielectrophoresis through the driving electrode layer 430 for moving the large-diameter bioparticles (e.g., blood cells) away from the central electrode 431, and generate an AC electroosmosis EF1 for gathering up the small-diameter bioparticles (e.g., bacteria) towards the central electrode 431, thereby achieving the effects of separating and gathering up the bioparticles as disclosed in FIG. 1C.

Figure 5:
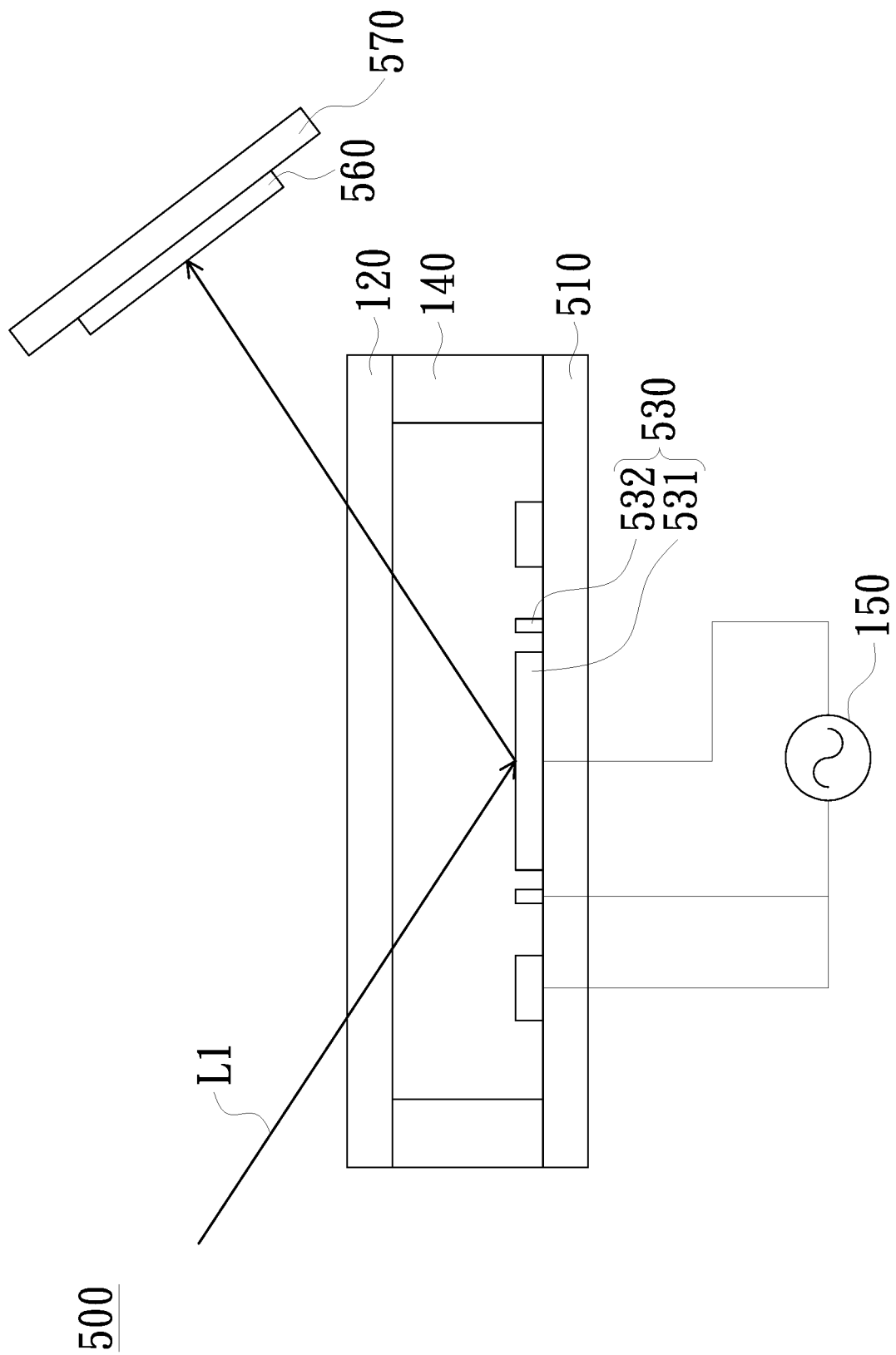
FIG. 5 is a schematic cross-sectional view of a photoelectrical device according to another preferred embodiment of the present invention.

FIG. 5 is a schematic cross-sectional view of the photoelectrical device according to another preferred embodiment of the present invention. Please refer to FIG. 5, a photoelectrical device 500 of the present embodiment is similar to the photoelectrical device 100 shown in FIG. 1A. For example, both of the photoelectrical devices 100 and 500 also include the same elements, and the methods of both for the efficacy and concentration detection are the same, and thus the similarities will not be described again. However, both the photoelectrical devices 100 and 400 of the aforementioned embodiments are transmissive detection devices, and the photoelectrical device 500 shown in FIG. 5 is a reflective detection device.

Specifically, a driving electrode layer 530 included in the photoelectrical device 500 is a metal layer, and therefore the driving electrode layer 530 is opaque and can reflect light. The photoelectrical device 500 can include a substrate 510, which can be a non-transparent substrate, and the driving electrode layer 530 is disposed on the substrate 510. The driving electrode layer 530 includes a central electrode 531 and a peripheral electrode pattern 532. The wiring pattern of both the central electrode 531 and the peripheral electrode pattern 532 can be the same as that of the central electrode 131 and the peripheral electrode pattern 132 shown in FIG. 1B, or can be the same as that of the central electrode 431 and the peripheral electrode pattern 432 shown in FIG. 4B.

The photoelectrical device 500 further includes a circuit substrate 570, wherein a photoelectric conversion layer 560 is formed on the circuit substrate 570. The material of the photoelectric conversion layer 560 can include silicon, such as amorphous silicon or polycrystalline silicon, and both the photoelectric conversion layer 560 and the circuit substrate 570 can be integrated into one solar panel. When the light detecting beam L1 is obliquely incident on the photoelectrical device 500, the light detecting beam L1 passes through the transparent cover plate 120 and the particle cluster (the particle cluster P10 shown in FIG. 1C) located on the central electrode 531 sequentially. Afterwards, since the driving electrode layer 530 is a metal layer, the central electrode 531 can reflect the light detecting beam L1 to the photoelectric conversion layer 560 so that the photoelectric conversion layer 560 can also generate an electric current according to the light detecting beam L1 it has received. In this way, the photoelectrical device 500 can also perform a method for concentration detection as shown in FIG. 2C to detect the concentration of the target bioparticles P11 in the fluid sample. Alternatively, the photoelectrical device 500 can also detect the effectiveness of an antibiotic on bacteria.

In summary, the photoelectrical device of the present invention can gather up the target bioparticles at one place (such as the central electrode), and can also separate at least two different bioparticles (such as bacteria and blood cells). Therefore, the photoelectrical device of the present invention not only can detect purified samples, but can also detect unpurified mixture samples such as blood, urine, perspiration and milk.

Secondly, the photoelectrical device of the present invention can directly detect the fluid samples having a low bacterial concentration, for example, samples having a concentration of below $10^8$ CFU/ml. In terms of antibiotic effectiveness analysis, the photoelectrical device of the present invention can analyze samples with an initial bacterial density of only $6\times10^4$ CFU/ml, and can discriminate bacterial concentration differences of samples that have been incubated for at least 3 hours (e.g., 4 hours) (incubation period). In comparison with the conventional optical analysis instruments that take more than one day of a long period of bacterial incubation to be effectively identified. The present invention can detect the differences in relatively micro-bacterial concentrations in a relatively short incubation time, and significantly shorten the detection time in order to effectively accelerate the bacterial concentration detection and antibiotic effectiveness analysis, thereby contributing greatly and progressively to disease diagnosis, treatment and antibiotics development.

Note that the specification relating to the above embodiments should be construed as exemplary rather than as limitative of the present invention, with many variations and modifications being readily attainable by a person of average skill in the art without departing from the spirit or scope thereof as defined by the appended claims and their legal equivalents.

What is claimed is:

1. A photoelectrical device for concentration detection adapted to detect a concentration of a plurality of target bioparticles in a fluid sample, the photoelectrical device comprising:
   a light source, adapted to emit a light detecting beam;
   a substrate, having an upper surface;
   a driving electrode layer, disposed on the upper surface of the substrate and comprising a central electrode;
   an AC power source, electrically connected to the driving electrode layer; and
   a photoelectric conversion element, disposed oppositely to the driving electrode layer;
   wherein the substrate further has a lower surface opposite to the upper surface, the photoelectric conversion element is disposed on the lower surface of the substrate, the substrate is a transparent plate, and both the driving electrode layer and the photoelectric conversion element are transparent conductive films;
   wherein the light detecting beam irradiates on the photoelectric conversion element after passing through the driving electrode layer and the substrate, the fluid sample is adapted to be disposed on the upper surface of the driving electrode layer, the AC power source is used to generate a non-uniform alternating electric field in the fluid sample on the upper surface of the driving electrode layer, the non-uniform alternating electric field drives the target bioparticles to gather up on the central electrode to form a particle cluster, the photoelectric conversion element is used to receive the light detecting beam after passing through the particle cluster, the photoelectric conversion element outputs an electric current based on the light detecting beam, and the electric current changes as a concentration of the target bioparticles changes; and
   wherein the photoelectrical device further comprises a peripheral electrode located around the central electrode, and the central electrode is not in contact with the peripheral electrode.

2. The photoelectrical device according to claim 1, further comprising a measurement electrode, wherein the measurement electrode is connected to the photoelectric conversion element and used to transmit the electric current.

3. The photoelectrical device according to claim 1, wherein a material of the photoelectric conversion element comprises metallic oxides or silicon.

4. The photoelectrical device according to claim 1, further comprising a transparent cover disposed oppositely to the substrate, wherein the driving electrode layer faces the transparent cover, and a detecting space is formed between the central electrode and the transparent cover.

5. The photoelectrical device according to claim 4, further comprising a transparent electrode layer formed on the transparent cover, wherein the transparent electrode layer and the driving electrode layer face each other, and the transparent electrode layer is electrically connected to the AC power source.

6. The photoelectrical device according to claim 1, wherein the peripheral electrode comprises:
   a first ring electrode, surrounding the central electrode by using the central electrode as a center; and
   a second ring electrode, surrounding the central electrode and the first ring electrode by using the central electrode as a center, wherein the first ring electrode and the second ring electrode are interdigiated and do not contact.

7. The photoelectrical device according to claim 1, wherein the peripheral electrode comprises:
   a ring electrode, surrounding the central electrode by using the central electrode as a center; and
   a plurality of auxiliary electrodes, connected with the ring electrode and extending radially from the ring electrode.

* * * * *